United States Patent [19]
Becker et al.

[11] Patent Number: 6,165,152
[45] Date of Patent: Dec. 26, 2000

[54] CATHETER WITH A FLEXIBLE TIP AND TAPER AND METHOD OF MANUFACTURE

[75] Inventors: Jon A. Becker, Dublin; Richard J. Saunders, Redwood City, both of Calif.

[73] Assignee: Advanced Cardiovascular Systems, Inc., Santa Clara, Calif.

[21] Appl. No.: 09/151,490

[22] Filed: Sep. 11, 1998

[51] Int. Cl.⁷ .................................................. A61M 29/00
[52] U.S. Cl. ........................................ 604/96.01; 604/523
[58] Field of Search ..................................... 604/264, 523, 604/96, 544, 96.01; 606/192, 194

[56] References Cited

U.S. PATENT DOCUMENTS

| | | | |
|---|---|---|---|
| 4,259,960 | 4/1981 | Taylor | 128/394 B |
| 4,579,554 | 4/1986 | Glassman | 604/102 |
| 4,717,379 | 1/1988 | Ekholmer | 604/43 |
| 4,776,846 | 10/1988 | Wells | 604/161 |
| 4,959,058 | 9/1990 | Michelson | 604/280 |
| 4,973,321 | 11/1990 | Michelson | 604/280 |
| 4,985,022 | 1/1991 | Fearnot et al. | 604/282 |
| 5,409,469 | 4/1995 | Schaerf | 604/282 |
| 5,437,288 | 8/1995 | Schwartz et al. | 128/772 |
| 5,599,319 | 2/1997 | Stevens | 604/264 |
| 5,645,528 | 7/1997 | Thome | 604/96 |
| 5,647,846 | 7/1997 | Berg et al. | 604/93 |
| 5,662,622 | 9/1997 | Gore et al. | 604/282 |
| 5,762,631 | 6/1998 | Klein | 604/171 |
| 5,899,890 | 5/1999 | Chiang et al. | 604/264 |
| 5,911,715 | 6/1999 | Berg et al. | 604/525 |
| 5,947,939 | 2/2000 | Mortier et al. | 604/280 |
| 5,989,230 | 11/1999 | Frassica | 604/264 |
| 6,024,730 | 2/2000 | Pagan | 604/264 |

*Primary Examiner*—Wynn Wood Coggins
*Assistant Examiner*—Cris Rodriguez
*Attorney, Agent, or Firm*—Heller Ehrman White & McAuliffe LLP

[57] ABSTRACT

A method of forming a catheter shaft having a flexible section by selective removal of catheter shaft material using laser radiation, and a catheter produced therefrom. The laser radiation is of an ultraviolet wavelength. The catheter shaft is made more flexible without a disadvantageous decrease in column strength by operating the laser in the UV, which allows for machining recess patterns with smooth and repeatable recess surfaces while producing little or no thermal or mechanical effects on the remaining adjacent polymeric material.

8 Claims, 3 Drawing Sheets

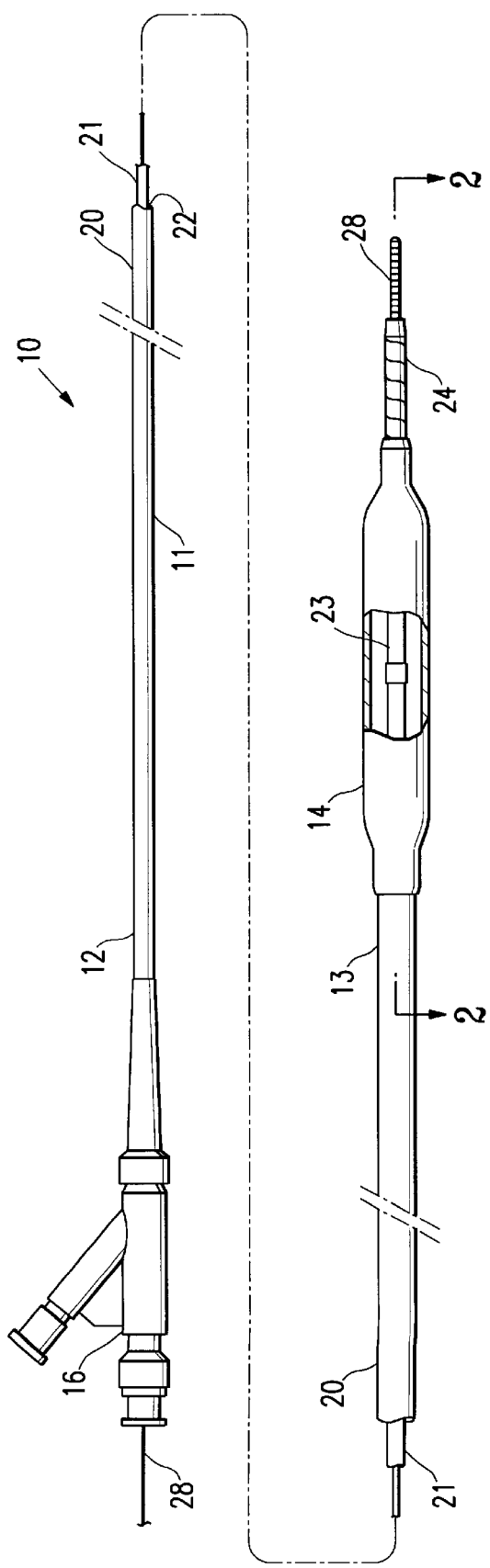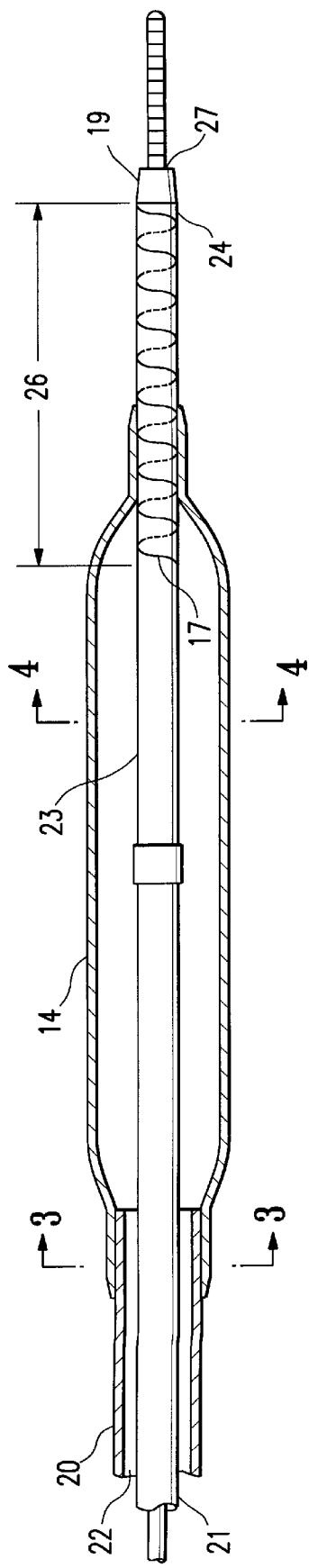
FIG. 1
FIG. 2

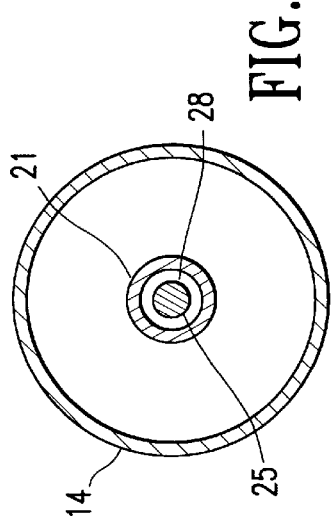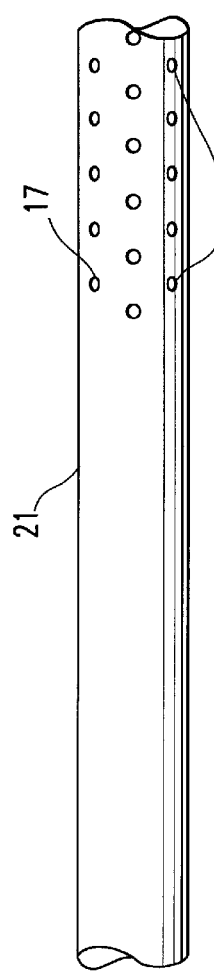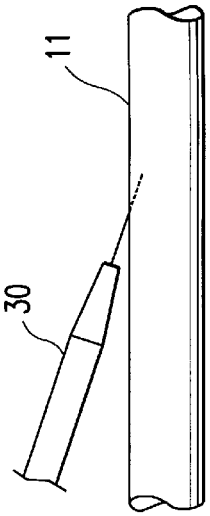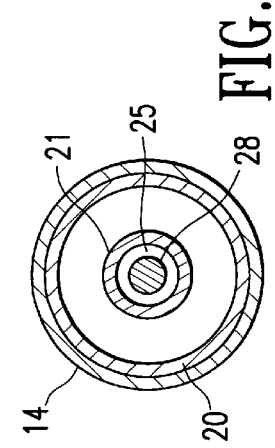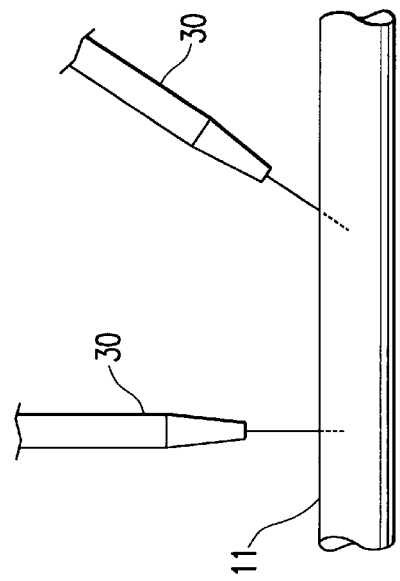

CATHETER WITH A FLEXIBLE TIP AND TAPER AND METHOD OF MANUFACTURE

BACKGROUND OF THE INVENTION

The invention relates to the field of intravascular catheters, and more particularly to a method of selectively removing material from a catheter shaft to produce a strong and flexible dilatation catheter shaft.

Percutaneous intravascular procedures, such as percutaneous transluminal coronary angioplasty (PTCA), were developed to open blocked vessels with as little trauma as possible. In PTCA procedures a guiding catheter having a preformed distal tip is usually percutaneously introduced into the patient's femoral artery by means of a conventional Seldinger technique and retrogradely advanced therein until the distal portion of the guiding catheter is located within the patient's ascending aorta with distal tip of the guiding catheter seated in the ostium of a desired coronary artery. The proximal end of the guiding catheter is torqued from outside the patient to guide distal tip of the guiding catheter into the desired ostium. A guidewire is positioned within an inner lumen of an dilatation catheter and then both are advanced through the guiding catheter to its distal end. The guidewire is first advanced out of the distal end of the guiding catheter into the patient's coronary artery until the distal end of the guidewire crosses a lesion to be dilated. Then the dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with liquid one or more times to a predetermined size at relatively high pressures (e.g. greater than 4 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter can be removed therefrom.

Commercially available intravascular balloon catheters used for angioplasty and other vascular procedures usually comprise an elongated shaft with an inflatable dilatation member on a distal portion of the shaft and an adapter on the proximal end of the shaft for the delivery of inflation fluid through an inner lumen extending through the catheter shaft to the interior of the inflatable dilatation member. Typically, the balloon catheter has an outer tubular member with a distal extremity terminating within the balloon interior and an inner tubular member with a distal extremity extending through and slightly beyond the distal end of the balloon. The annular space between the inner and outer members defines the inflation lumen in communication with the balloon interior. Alternatively, a single catheter shaft provided with a plurality of lumens can be used in place of the inner and outer membered shaft. The catheter may be typically be provided with a distal tip that is flexible and tapered.

An essential step in PTCA is maneuvering the catheter over the guidewire until the balloon on the distal end of the catheter is in the desired location within the arterial occlusion. However, maneuvering the dilatation catheter over a guidewire through small branched vessels and through the stenosis requires a distal end that is both flexible and strong, to provide a catheter which is trackable and pushable.

The removal of material from the distal tip of a dilatation catheter to increase its flexibility is disclosed in U.S. Pat. No. 4,960,410 (Pinchuk) and U.S. Pat. No. 5,514,108 (Stevens). When removing material from a catheter shaft, one difficulty has been precisely forming a cut in the catheter shaft. Mechanical and thermal cutting methods disadvantageously displace shaft material during the cutting procedure, which results in an increase in the shaft diameter. For example, mechanical cutting displaces or deforms the shaft material by physically pushing the material to one side. Thermal processing methods of cutting a shaft melt the material, and as the melted material cools it coalesces into spherical beads that are typically greater than about 0.0002 to 0.0005 inches. Such beads form at the edge of the cut, and thus increase the shaft outer diameter from its original dimension at the junction between the cut and uncut material. In the formation of a distal tip taper, previous methods, such as sanding or heat forming, may also leave rough surfaces or displaced material. Such displaced material or rough surfaces undesirably increases the shaft profile and stiffness.

What has been needed is a method of selectively removing material from a polymeric substrate in a precise and controllable manner to produce a flat cut surface without displacing shaft material that increases the shaft outer diameter. The present invention satisfies these and other needs.

SUMMARY OF THE INVENTION

The invention is directed to a method of forming a catheter shaft by precise removal of catheter shaft material using laser radiation in an ultraviolet region, and a catheter produced therefrom. Using the method of the invention, a catheter shaft can be prepared having a recess or a tapered section with a smooth surface. Additionally, the surface of the shaft adjacent to the recess or tapered section is undisturbed because the method of the invention removes shaft material without significantly affecting, either mechanically or thermally adjacent regions, e.g., increasing the shaft outer diameter from its original dimension. Recesses made into the shaft wall result in improved shaft flexibility while maintaining a significant amount of the original column strength of the shaft.

The method of the invention generally includes removal of catheter shaft material in various patterns and regions along the axis of the shaft to adjust the shaft performance characteristics. In accordance with the invention, the catheter shaft material is removed using laser radiation particularly in the ultraviolet region having a wavelength from about 4 to about 400 nanometers (nm), preferably from about 190 to about 360 nm. Laser radiation in this wavelength vaporizes the polymer material to be removed, while producing little or no mechanical or thermal effects on the remaining adjacent material. Because the material is vaporized by laser radiation at UV wavelengths, the cut material is not physically displaced or deformed as it is when mechanical cutting methods are used. Thermal effects are minimized or eliminated by the laser radiation in the UV wavelengths, the polymeric material is not melted, and the beading up of melted polymeric material produced by thermal processing is avoided. Therefore, a recess produced using the UV wavelengths of the invention has a smooth surface and the adjacent polymeric material is undisturbed so that the original outer diameter of the shaft is not increased.

Precise control over the removal of shaft material is needed in order to vary the catheter characteristics in a repeatable and controllable manner. Precise control is also needed when forming a taper in the shaft distal end, so that a smooth transition in the shaft outer diameter along the length of the catheter is produced.

The laser wavelength and optical set-up for imaging the laser beam on the catheter shaft is selected to precisely control the removal of material in a selected area. The optimal wavelength depends upon the material used to form the catheter shaft. Additionally, the depth of removal of the material is controllable by selection of one or more parameters such as the laser power, pulse rate, removal area size and shape, and the speed movement of the beam or material during the removal. However, the laser radiation must be applied to a given unit area of material, at sufficiently low power, so that the shaft material does not melt during the removal.

The pattern of the recess and the region from which the material is removed affects the performance characteristics of the catheter produced using the method of the invention. One presently preferred embodiment of the invention involves removal of shaft material from a distal section of the shaft to form a more flexible distal end. One aspect of the invention involves the removal of shaft material from the distal end of an inner tubular member of a balloon catheter, although the invention includes the removal of material from other sections of the catheter shaft.

The recess in the shaft preferably extends only partially through the wall of the shaft. Additionally, the shaft material may be removed from the outer surface of the shaft to form an outer diameter concentric with an inner diameter of the shaft or a tapered shaft section having a decreasing outer diameter.

The catheter shaft material is a polymeric material which vaporizes upon application of UV laser radiation in accordance with the method of the invention. Such polymer materials include those thermoplastic materials typically used in the fabrication of catheters, such as polyethylene and PVC. Additionally, the shaft may be made by co-extrusion of different polymeric materials.

A recess in a catheter shaft produced using the method of the invention has a smooth surface, and the surface of the shaft adjacent to the recess or tapered section is undisturbed and is in its original uniform and smooth conditions because the recess is formed without increasing the shaft outer diameter from its original dimension. Such a catheter has excellent trackability due to the adjustments made to the shaft flexibility without a disadvantageous loss of compressive strength along the axis of the shaft. Additionally, a catheter having a flexible and low profile distal tip taper can be produced using the method of the invention. These and other advantages of the invention will become more apparent from the following detailed description of the invention and the accompanying exemplary drawings.

BRIEF DESCRIPTION OF THE DRAWINGS

FIG. 1 is an elevational view of balloon catheter embodying features of the invention.

FIG. 2 is an enlarged view of the distal end of the balloon catheter shown in FIG. 1 taken along lines 2—2, showing the cut out regions formed by the method of the invention.

FIG. 3 is a transverse cross section of the catheter of FIG. 2 taken along lines 3—3.

FIG. 4 is a transverse cross section of the catheter of FIG. 2 taken along lines 4—4.

FIG. 5 is an enlarged view of a catheter shaft embodying features of the invention.

FIGS. 6 and 7 illustrate laser radiation application to a catheter shaft during removal of catheter shaft material.

DETAILED DESCRIPTION OF THE INVENTION

Figure 8:
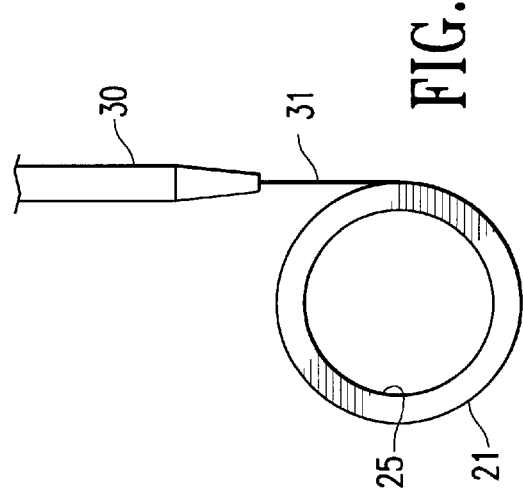
FIG. 8 illustrates laser radiation application transverse with a catheter shaft to machine grooves, or pits in the catheter shaft.

FIG. 1 illustrates a balloon catheter 10 having an elongated catheter shaft 11 having a proximal end 12 and a distal end 13, an inflatable balloon 14 on a distal section proximal to the distal end of the catheter shaft, an adapter 16 mounted on the proximal end 12, and at least one recess 17 formed in a wall of the shaft 11 by application of laser radiation.

One significant benefit of using a UV laser to form the recess 17 is that a recess with a smooth surface is formed without increasing the shaft diameter or otherwise mechanically or thermally affect adjacent polymeric materials. Because the material is not physically pushed or melted during the removal, the increase in the shaft diameter which is caused by physical displacement of material or beading of melted material is avoided. By controlling the removal of material, the method of the invention provides a means of precisely and repeatably affecting the flexibility and strength along a region of the shaft axis.

In the embodiment shown in FIG. 1, the shaft 11 comprises an outer tubular member 20 and an inner tubular member 21 disposed within the outer tubular member, and defining, with the outer tubular member, inflation lumen 22 in fluid communication with the balloon interior. The inner tubular member 21 has an outer surface 23 and a distal end 24 and an inner lumen 25 extending distally to a port 27 in the distal end to the balloon. Guidewire 28 is slidably disposed within a lumen of the inner tubular member 21.

The pattern, density, area and location of the material removed affects the flexibility and compressive strength of the catheter shaft 11, and are therefore chosen based on the desired shaft performance characteristics. The recess 17 may form grooves, or pits or depressions in the shaft, and in various patterns including continuous or multiple spirals, rings, and semi-circles, and the like. In the embodiment illustrated in FIG. 2, the recess 17 forms a continuous spiral 26 in the shaft 11. FIG. 5 illustrates an alternative embodiment of the invention in which the recess 17 forms multiple pits 27 in the outer surface of the catheter inner tubular member 21. Additionally, recess may form tapering in shaft outer diameter, and preferably a tapered distal tip 19, as illustrated in FIG. 2.

The UV laser radiation allows for recess sizes from about 0.25 μm to about several square centimeters, and for non-uniform dimensioned areas such as 0.05 mm×0.5 mm (0.002×0.02 inch). The width of the recess in the wall of the shaft is typically about 0.25 μm to about 1.0 mm, and the depth of the recess into the shaft wall is typically about 0.25 μm to about 0.5 mm. The presently preferred laser power ranges from about 10 mJ to about 20 mJ, and the pulse rate ranges from about 10 pps to about 100 pps.

In one example, the invention comprises a balloon catheter with a flexible distal section formed by a recess 17 on a distal portion of the inner tubular member. Preferably, the recess 17 is located from a point proximal to the distal end of the balloon, and extending toward, and possibly up to, the distal end of the shaft. The length of the catheter is generally from about 90 cm to about 150 cm. Typically, in forming a flexible distal shaft section or a tapered distal end, the recess extends along a section of the catheter ranging from about 1.5 mm to about 7 mm in length, and preferably about 2 to about 6 mm in length. The length of the section will vary depending on the degree of flexibility desired in the catheter.

Figure 9:
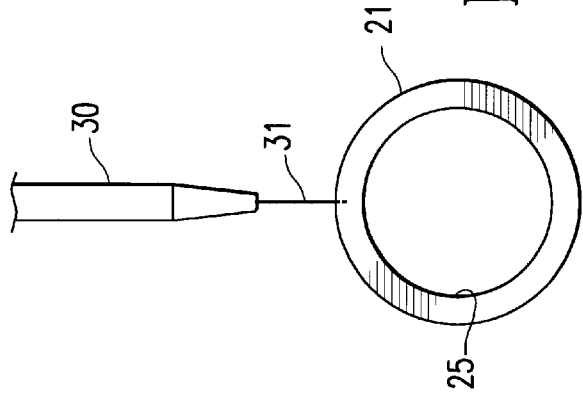
FIG. 9 illustrates laser radiation application tangential with a catheter shaft to machine an outer diameter concentric with an inner diameter or tapering in the catheter shaft.
Figure 10:
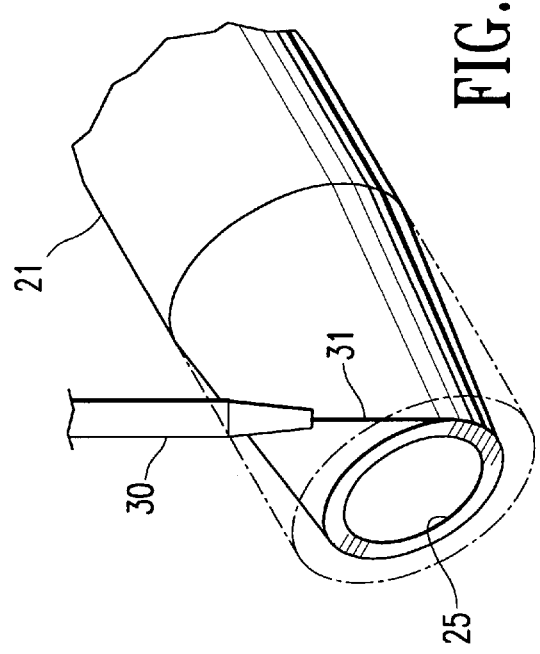
FIG. 10 illustrates laser radiation application tangential with a catheter shaft to machine tapering in the catheter shaft distal end.

In the method of the invention, a catheter having a polymeric elongated shaft 11 with a flexible section 18 is manufactured by a method comprising, forming at least one recess 17 in the shaft by applying laser radiation of an ultraviolet wavelength to an outer surface of the shaft to remove shaft material. The UV laser radiation may remove material both axially and radially from a catheter shaft 11. FIGS. 6 and 7 illustrates laser energy 31 being applied by laser 30 to the catheter shaft 1. As best illustrated in FIG. 8, showing a transverse cross-sectional view of a catheter shaft 11, the laser radiation 31 may be applied transverse to the shaft to form grooves or pits in the shaft 11. As illustrated in FIGS. 6 and 7, the transversely applied laser radiation may be applied perpendicular relative to the shaft longitudinal axis or at an acute angle relative to the shaft. The acute angle is typically about 10° to about 80° relative to the shaft. Alternatively, as illustrated in FIG. 9, the laser radiation may be applied tangentially to the shaft, to form a tapered distal section or form a shaft outer diameter concentric with an inner diameter by correcting nonuniformity in the shaft outer diameter. To form a tapered distal section, the laser is moved at an angle relative to the shaft longitudinal axis to remove an increasing amount of shaft material. FIG. 10 illustrates formation of a tapered distal tip, with the radiation focus tangential to the catheter shaft and moved longitudinally relative to the shaft at an angle to the shaft axis. The relative movement between the catheter and the laser is typically achieved by moving the catheter about a fixed laser.

While the laser wavelength is preferably within the ultraviolet region, within that region, the longest wavelengths are less absorptive and therefore less effective and shortest wavelengths are generally more difficult to produce, requiring very specific optics. The presently preferred wavelengths are from about 190 nm to about 360 nm, and most preferably are selected from the group consisting of 248 nm, 266 nm, and 355 nm. Lasers used in the invention must be able to produce radiation in the UV region. Suitable lasers include a pulsed eximer laser, such as a KrF, XeF, KrCl, XeCl or XeBr laser, and non-linear harmonic crystals optically pumped by a laser with an output that is continuous wave, pulsed, Q-switched, or modulated. The presently preferred laser source is an eximer laser or a Nd/YAG laser. Selection of the wavelength within the ultraviolet region and the appropriate optical set-up for imaging the laser beam on the catheter shaft allows precise control over the removal of material in a selected area or pattern.

While the present invention has been described herein in terms of certain preferred embodiments, modifications and improvements may be made to the invention without departing from the scope thereof. For example, while the formation of a gradual taper in the catheter shaft distal end was described, the method of the invention could also be used to form abrupt stepped down sections in a catheter shaft. Additionally, while the invention is described herein in terms of an inner and outer membered balloon catheter, it should be understood that the invention is not limited to use with balloon catheters, or catheter designs having inner and outer shaft members.

What is claimed is:

1. A balloon catheter comprising an elongated shaft formed of a polymeric material having a proximal and a distal end and a balloon mounted on a portion thereof, an outer diameter, a lumen extending along a length thereof, and having a flexible shaft section with an outer surface having a first uniform smoothness and including at least one recessed area formed in at least part of the shaft outer surface and extending from a point located distally of a proximal end of the balloon to a point located distally of a distal end of the balloon, the outer surface adjacent the at least one recessed area having a smoothness substantially the same as the first smoothness.

2. The catheter of claim 1 wherein the recess in the shaft has a smooth surface.

3. The catheter of claim 1 wherein the recess does not extend through the shaft to the shaft lumen.

4. The catheter of claim 1 wherein the recess forms a groove in the shaft.

5. The catheter of claim 1 wherein the recess forms a spiral along the shaft.

6. The catheter of claim 1 wherein the recess forms a pit in the shaft.

7. The catheter of claim 1 wherein the recess has a width of about 0.25 µm to about 1.0 mm.

8. The catheter of claim 1 wherein the recess has a depth into the shaft of about 0.25 µm to about 0.5 mm.

\* \* \* \* \*